(12) United States Patent
Kobayashi (10) Patent No.: US 9,737,708 B2
(45) Date of Patent: Aug. 22, 2017

(54) RESPIRATORY ABNORMALITY IMPROVEMENT APPARATUS

(71) Applicant: TECHNO LINK CO., LTD., Niigata (JP)

(72) Inventor: Tatsuyuki Kobayashi, Niigata (JP)

(73) Assignee: Techno Link Co., Ltd., Nagata (JP)

( * ) Notice: Subject to any disclaimer, the term of this patent is extended or adjusted under 35 U.S.C. 154(b) by 58 days.

(21) Appl. No.: 14/520,879

(22) Filed: Oct. 22, 2014

(65) Prior Publication Data
US 2015/0328451 A1  Nov. 19, 2015

(30) Foreign Application Priority Data
May 16, 2014 (JP) .................................. 2014-102553

(51) Int. Cl.
*A61N 1/36* (2006.01)
*A61N 1/04* (2006.01)
(Continued)

(52) U.S. Cl.
CPC ......... *A61N 1/3601* (2013.01); *A61N 1/0492* (2013.01); *A61B 5/0816* (2013.01); *A61B 5/4818* (2013.01); *A61N 1/0452* (2013.01)

(58) Field of Classification Search
None
See application file for complete search history.

(56) References Cited

U.S. PATENT DOCUMENTS 5,190,053 A  3/1993  Meer
2006/0247729 A1*  11/2006  Tehrani ............... A61N 1/3601
607/42
(Continued)

FOREIGN PATENT DOCUMENTS

CN  102481127  7/2015
EP  1 815 882 A1  8/2007
(Continued)

OTHER PUBLICATIONS

JIS C 6310-1986 Explanation of Low Frequency Therapy Equipment published on Dec. 20, 2011.
(Continued)

*Primary Examiner* — Erica Lee
(74) *Attorney, Agent, or Firm* — Fox Rothschild LLP; Robert J. Sacco; Carol E. Thorstad-Forsyth (57) ABSTRACT

Provided is a respiratory abnormality improvement apparatus capable of effectively improving respiratory abnormality during sleep. The present invention is a respiratory abnormality improvement apparatus for applying a stimulus signal generated in a stimulus generating unit to a patient as an electric stimulus. Here, the apparatus includes a respiration detection unit for detecting a respiratory condition of the patient. Particularly, the stimulus generating unit is so configured that a first stimulus signal generated at a current level preset at a given time, and a second stimulus signal of a current level different from that of the first stimulus signal are generated as stimulus signals to an electrode member worn by the patient based on a detection signal from the respiration detection unit when the patient has been judged to be under a respiratory abnormality condition.

12 Claims, 6 Drawing Sheets

(51) Int. Cl.
    *A61B 5/08*      (2006.01)
    *A61B 5/00*      (2006.01)

(56)         References Cited

U.S. PATENT DOCUMENTS

2007/0118183 A1*  5/2007  Gelfand ............... A61N 1/3601
                                                         607/42
2008/0188904 A1   8/2008  Tehrani et al.
2012/0125337 A1   5/2012  Asanoi
2012/0192874 A1   8/2012  Bolea et al.

FOREIGN PATENT DOCUMENTS

FR        2 305 168 A1    10/1976
JP       2005-537819 A    12/2005
JP           4960704 B2    6/2012
JP           5535405 B2    7/2014
WO         03/086531 A2   10/2003
WO        2005/002663      1/2005
WO        2006/054359 A1   5/2006
WO        2013/008541 A1   1/2013

OTHER PUBLICATIONS

Office Action dated Jul. 15, 2014 in Japanese Patent Application No. 2014-102553 and English translation.
Office Action dated Dec. 25, 2015 for Taiwan patent application No. 103134149 (translation attached).
European Search Report dated Sep. 11, 2015 for application No. EP 14 00 3611.

\* cited by examiner

RESPIRATORY ABNORMALITY IMPROVEMENT APPARATUS

BACKGROUND OF THE INVENTION

Field of the Invention

The present invention relates to a respiratory abnormality improvement apparatus for preventing or alleviating respiratory abnormalities such as sleep apnea and infrequent respiration during sleep by applying an electric stimulus to a patient's living body.

Description of Related Art

As a respiratory abnormality improvement apparatus for treating respiratory abnormalities during sleep by applying an electric stimulus to a mentalis muscle, there are proposed a method for applying an electric stimulus in synchronization with sleep apnea and infrequent respiration during sleep; and a method for continuously applying a monotonous electric stimulus regardless of conditions of the sleep apnea and infrequent respiration during sleep.

As the former method, U.S. Pat. No. 5,190,053, for example, discloses a configuration in which a respiratory effort and an intrathoracic pressure of a patient are monitored by a sensor, and when it is found through a comparison between a condition detected by the sensor and a threshold that a patient had fallen into a respiratory difficulty, electric signals are applied for a given period of time to stimulate the patient's muscle. Further, as the latter method, Japanese Patent No. 4960704 discloses a configuration in which a stimulus signal out of synchronization with an apneic condition is applied to a patient in such a manner as to alternate, for a given length of time, a conduction period where a group of electric pulses composed of a plurality of electric pulses is generated and a break period where no group of electric pulses is generated.

SUMMARY OF THE INVENTION

As for the abovementioned conventional techniques, the former which is a synchronization method has a problem that concurrently with the detection of apnea, a current is applied as an electric signal to a patient less experienced in an electric stimulus, and hence patient's cutaneous nerves excessively respond to cause such considerable cases as to lead to awakening even by the application of a low current.

Further, the latter which is a non-synchronization method also has a problem that a maximum critical current for not causing an arousal during sleep is output with a monotonous rhythm (by means of a fixed timer), and hence a patient's body becomes habituated to the current, thus resulting in a lack of stimulus to the patient regardless of the fact that applied is a current slightly lower than the arousal-causing critical current. In this case, an integrated current value (time multiplied by a current value) tends to enlarge beyond necessity, causing a negative effect due to a long-period conduction. Moreover, there exists an individual difference in determining the arousal-causing critical current, thereby resulting in a difficulty in setting an optimal critical current.

For reference, when suddenly applying a current to a human body as a living body, a human body (nerve) not experienced in an electric stimulus provokes an excessive response. For this reason, a low-frequency therapy equipment or the like acting as a normal electric stimulating apparatus operates in such a fashion that a zero start mode that starts with a stimulus current set at zero at the start of therapy is determined and even in performing an interval conduction in which the stimulus current is intermittently conducted, an abrupt increase in current causes a large pain, and therefore the stimulus current is moderately increased.

Conversely, if continuously applying a strong electric stimulus, the human body (or nerve) becomes habituated to the stimulus to become anesthetic in turn, so that this stimulus becomes insufficient to the human body unless an even larger electric stimulus is applied.

Therefore, in view of the problem described above, it is an object of the present invention to provide a respiratory abnormality improvement apparatus capable of applying, when respiratory abnormality has occurred, an appropriate electric stimulus-until the abnormality is improved to thereby enable the respiratory abnormality during sleep to be effectively improved while normally applying such an electric stimulus as not to debase a sleeping quality to prevent the respiratory abnormality.

The present invention is a respiratory abnormality improvement apparatus for applying to a patient a stimulus signal generated in a stimulus generating unit as an electric stimulus, including: a detection unit for detecting a respiratory condition of the patient, in which the stimulus generating unit is configured in a manner such that the stimulus generating unit generates, as the stimulus signal, a first stimulus signal of a current level preset at a given time; and generates, as the stimulus signal, a second stimulus signal of a current level different than the current level of the first stimulus signal based on a detection signal from the detection unit when the patient is judged to be under a respiratory abnormality condition. Specifically, the stimulus generating unit is configured in a manner such that each of the first and second stimulus signals repeats a conduction period where an electric pulse group having a current level greater than a given level is generated and a break period where an electric pulse group having a current level not greater than a given level is generated or no electric pulse group is generated. More specifically, as for each conduction period, there exist a first interval where the current level of the stimulus signal increases and rises in a manner such that a rate of increase becomes gradually moderate with time; and a second interval where the current level of the stimulus signal becomes constant after the first interval. Also, the stimulus generating unit is configured in a manner such that inserted into the first or second interval of the conduction period is a dither allowing either the current level or frequency of the stimulus signal to repeatedly increase and decrease; or both the current level and frequency of the stimulus signal to repeatedly increase and decrease.

In the aforementioned structure, the stimulus generating unit may be configured in a manner such that, during the aforementioned break period, the current level is lowered within a range from 0 to a value that causes no muscle tension on the patient.

Further, the stimulus generating unit may be configured in a manner such that, during the break period at the time of generating the first stimulus signal, the current level of the electric pulse is maintained at a constant value other than 0; and that, during the break period at the time of generating the second stimulus signal, the current level of the electric current pulse group is set to be 0.

Furthermore, the stimulus generating unit may be configured in a manner such that, during the conduction period at the time of generating the first stimulus signal, the dither is not inserted into the first interval but only into the second interval; and that, during the conduction period at the time of generating the second stimulus signal, the dither is to be inserted from during the first interval through the second interval.

Furthermore, the stimulus generating unit may be configured in a manner such that, during the period where the dither is inserted, the current level of the stimulus signal rises in a manner such that the rate of increase becomes gradually moderate with time.

Furthermore, the stimulus generating unit may be configured in a manner such that, during the dither insertion period at the time of generating the first stimulus signal, the frequency of the stimulus signal repeatedly increases and decrease only during the period where the current level of the stimulus signal rises.

Furthermore, the stimulus generating unit may be configured in a manner such that, during the dither insertion period at the time of generating the second stimulus signal, the frequency of the stimulus signal repeatedly increases and decreases only during the period where the current level of the stimulus signal is maintained constant before rising.

Furthermore, the apparatus may include: an electrode member that is attached to the patient and used to output the stimulus signal to the patient; and an electrode-member monitoring unit for detecting an abnormal condition by monitoring a current and a voltage that are applied to the electrode member.

Furthermore, the apparatus may include: an electrode member that is attached to the patient and used to output the stimulus signal to the patient, the electrode member having at least one electrode to which the stimulus signal is supplied and a moisture permeable material-made adhesive cover member to which the electrode is attached.

Furthermore, the apparatus may include: an electrode member that is attached to the patient and used to output the stimulus signal to the patient, the electrode member having at least one electrode to which the stimulus signal is supplied and a vented adhesive cover member to which the electrode is attached.

Furthermore, the apparatus may include: an electrode member that is attached to the patient and used to output the stimulus signal to the patient; and a pair of cords connecting the stimulus generating unit and the electrode member, in which the electrode member includes a pair of electrodes to which the stimulus signal is supplied and an adhesive cover member to which the electrodes are attached, and in which the pair of the cords are drawn from different sides of the pair of the electrodes.

Furthermore, the stimulus generating unit may be configured in a manner such that the stimulus signal is capable of being applied to the patient everyday.

According to the present invention, such an electric stimulus as not to debase a sleeping quality of the patient is usually applied as the first stimulus signal from the stimulus generating unit, and thereby without applying the electric stimulus of an excessively high current level and awakening the patient, the respiratory abnormalities such as apnea and infrequent respiration can be prevented or remarkably alleviated. Further, when a detection signal peculiar to apnea and infrequent respiration is output from the detection unit with the first stimulus signal being applied to the patient, a second stimulus signal, which increases the current level of the electric stimulus or changes the intensity of the current level, is applied to the patient until such a peculiar detection signal is no longer present or for a given period of time. In this manner, when the respiratory abnormalities occur, the second stimulus signal of a current level different from that of the first stimulus signal is applied as an appropriate electric stimulus until these abnormalities are improved, thus allowing the respiratory abnormalities of the patient during sleep to be effectively improved. Further, as for the stimulus generating unit, at the time of the rising of the conduction period, the stimulus signal is generated and outputted in a way such that the increasing rate of current level thereof gradually becomes moderate with time. Therefore, a strong pain can be prevented from occurring due to a rapid rising of the current level of the stimulus signal. In addition, during the conduction period of the stimulus signal, inserted is the dither allowing either the current level or frequency; or both the current level and frequency to be increased and decreased in a short period of time, thereby maintaining a stimulus feeling constant.

DETAILED DESCRIPTION OF THE INVENTION

With reference to accompanying drawings, hereunder is a description of a preferred embodiment of a respiratory abnormality improvement apparatus of the present invention.

Figure 1:
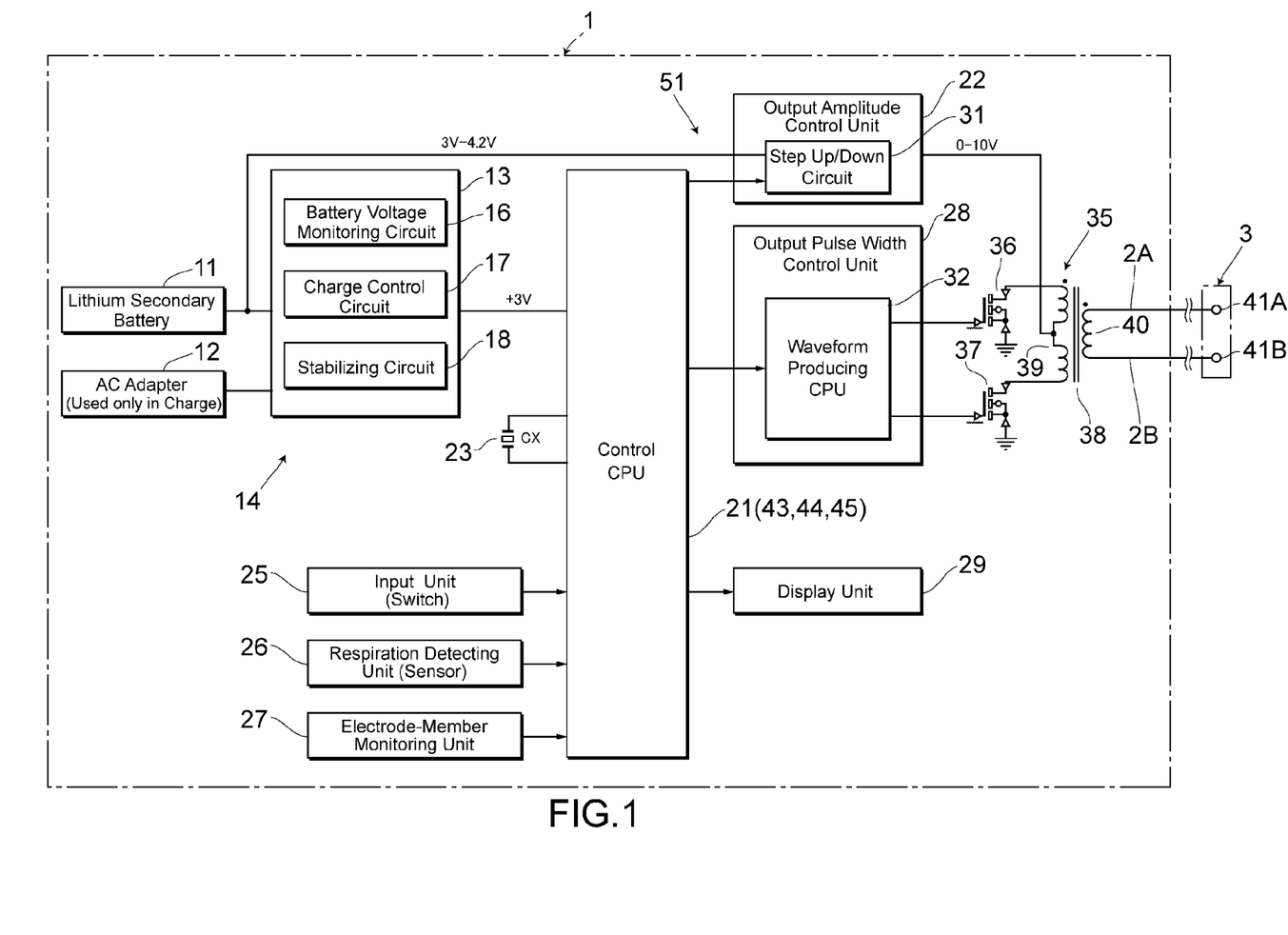
FIG. 1 is a block diagram illustrating an overall configuration of a respiratory abnormality improvement apparatus in the present invention.

FIG. 1 is a block diagram showing an overall configuration of the apparatus. In FIG. 1, the respiratory abnormality improvement apparatus of the present embodiment includes: a main body 1 serving as a principal part of the apparatus; and an electrode member 3 electrically connected to the main body 1 through a pair of cords 2A, 2B that serve as connecting members.

At first, a configuration of the main body 1 is described. A numerical symbol 11 denotes a chargeable and dischargeable lithium secondary battery; a numerical symbol 12 denotes an AC adapter for converting an alternative-current (AC) power drawn from a commercial power source outside the apparatus into a direct-current (DC) power to output this DC power; and a numeral symbol 13 denotes an electric power source unit electrically connected to the lithium secondary battery 11 and the AC adapter 12. The lithium secondary battery 11, the AC adapter 12 and the electric power source unit 13 compose an electric power supply unit 14 for supplying a given DC electric power to a control CPU 21 and an output amplitude control unit 22 that are described later.

The electric power source unit 13 includes: a battery voltage monitoring circuit 16 for monitoring a charging and a discharging voltages of the lithium secondary battery 11;

a charge control circuit 17 for controlling charging the lithium secondary battery 11; and a stabilizing circuit 18 for stabilizing a DC voltage from the lithium secondary battery 11 before outputting the same. Particularly, the AC adapter 12 of the present embodiment is to be connected to a commercial power source only when charging the lithium secondary battery 11. Once the DC power has been output from the AC adapter 12 to the electric power source unit 13, the charge control circuit 17 receives a monitored result from the battery voltage monitoring circuit 16 to charge the lithium secondary battery 11 with a given current and voltage. In contrast, when the AC adapter 12 is not connected to a commercial power source, a terminal voltage, e.g., DC 3V to 4.2V, generated in the lithium secondary battery 11 is directly output to the output amplitude control unit 22; and a stabilized DC voltage of, e.g., +3V is supplied to the control CPU 21 through the stabilizing circuit 18.

The control CPU 21 as a control unit operates by receiving a reference clock signal from a crystal oscillator 23 in addition to the DC voltage from the stabilizing circuit 18. Further, the control CPU 21 has, for example, a known input-output unit, a storage unit and a calculation processing unit that are built therein. Here, the control CPU 21 is so configured that a stimulus current of a given pattern is applied from the electrode member 3 to a human body (not shown) as a living body, in accordance with a control sequence stored in the storage unit.

Connected to input ports of the control CPU 21 are an input unit 25 composed of a plurality of switches, a respiratory detection unit 26 operating with a sensor and an electrode-member monitoring unit 27 for monitoring a condition of the electrode member 3. The input unit 25 instructs, for example, a level (amplitude) and time of the stimulus current as well as an output start and an output halt of the stimulus current. Instruction signals generated by manually operating the input unit 25 are imported into the control CPU 21. The respiration detection unit 26 includes a plurality of or a single sensor(s) for detecting, for example, accelerations, flows, sounds and degrees of oxygen saturation, such that the respiration detection unit 26 can sense, as a respiratory abnormality condition, either a condition where apnea and infrequent respiration has occurred or a condition where apnea and infrequent respiration seems to have occurred. The electrode-member monitoring unit 27 serves to monitor, in the main body 1, a current flowing through the electrode member 3 and a voltage applied thereto. The electrode-member monitoring unit 27 includes, for example, a current detecting unit and a voltage detecting unit in order to sense peeling of the electrode member 3, an electric short and breaking of wire.

Meanwhile, other than the aforementioned output amplitude control unit 22, an output pulse width control unit 28 and a display unit 29 composed of, for example, LEDs and LCDs are respectively connected to an output port of the control CPU 21. The output amplitude control unit 22 serves to produce a variable output signal for determining the amplitude of each electric pulse in the stimulus signal. Here, built in the output amplitude control unit 22 is a step-up/down circuit 31 that receives a first control signal from the control CPU 21, and then converts the terminal voltage from the lithium secondary battery 11 to a variable output signal of a range of, for example, DC 0V to 10V before outputting the same. Further, an output pulse width control unit 28 serves to generate a pulse output signal for determining an on-time and off-time of each electric pulse in the stimulus signal. Here, built in the output pulse width control unit 28 is a waveform producing CPU 32 that receives a second control signal from the control CPU 21, and then produces a pulse output signal of a given time width at a given timing before outputting the same.

A numerical symbol 35 denotes a stimulus signal producing unit that receives the variable output signal output from the output amplitude control unit 22 and the pulse output signal to be output to the output pulse width control unit 28; and then outputs to the electrode member 3 a stimulus signal repeating a conduction period where an electric pulse group having a current level greater than a given level (a first level L1 shown in FIG. 4 to FIG. 7) is continuously or intermittently generated and a break period where an electric having a current level pulse group not greater than a given level is generated or no electric pulse group is generated. The stimulus signal producing unit 35 of the present embodiment includes a transformer 38 whose primary and secondary sides are insulated, in addition to FETs 36, 37 as switching units. A center tap in a primary winding 39 of the transformer 38 is connected to a variable output signal line of the output amplitude control unit 22. One end of the primary winding 39 is connected to a drain of the FET 36 that is source-grounded, while the other end of the primary winding 39 is connected to a drain of the FET 37 that is source-grounded. Further, an electrode 41A of the electrode member 3 is connected to one end of a secondary winding 40 of the transformer 38 through one cord 2A, while another electrode 41B of the electrode member 3 is connected to the other end of the secondary winding 40 of the transformer 38 through the other cord 2B. Moreover, a plus-side pulse output signal from the control CPU 21 is supplied to a gate serving as a control terminal of the FET 36, while a minus-side pulse output signal from the control CPU 21 is supplied to a gate serving as a control terminal of the FET 37.

As a functional structure of a control sequence built in the storage unit, the control CPU 21 includes a first control signal generating unit 43, a second control signal generating unit 44 and an operating condition managing unit 45. The first control signal generating unit 43 generates a first control signal for determining an amplitude of a variable output signal. The second control signal generating unit 44 outputs the pulse output signal to the gate of one of the FETs 36, 37, and generates a second control signal for determining an on-time period and off-time period of the pulse output signal. The operating condition management unit 45 stores operating conditions of the stimulus signal output to the electrode member 3, displays these operating conditions on the display unit 29 if needed, and then receives an instruction signal from the input unit 25 to update and set the operating conditions. The operating conditions referred to here mean a current level of the stimulus signal when the respiration detection unit 26 detects no respiratory abnormality of a patient and a current level of the stimulus signal when the respiration detection unit 26 has detected a respiratory abnormality of the patient, other than the conduction and break periods of the group of the electric pulses described above.

Here, the first control signal is received from the first control signal generating unit 43 to output the variable output signal of a given voltage level from the output amplitude control unit 22 to the center tap of the primary winding 39 of the transformer 38, and a second control signal from the second control signal generating unit 44 is received to output a rectangular-waveform pulse output signal having a given on-time period and a given off-time period from the output pulse width control unit 28 to one of the FETs 36, 37. As a result, the stimulus signal is allowed to be generated in the secondary winding 40 of the transformer 38. That is, the control CPU 21 including the first control signal generating unit 43 and the second control signal generating unit 44, the output amplitude control unit 22, the output pulse width control unit 28, and the stimulus signal producing unit 35 including the FETs 36, 37 and the transformer 38 correspond to a stimulus generating unit 51 for applying the stimulus signal from the electrode member 3 to the patient as a living body.

The stimulus generating unit 51 receives from the respiratory detection unit 26 the respiratory abnormality condition of the patient wearing the electrode member 3, such that the stimulus generating unit 51 can control the intensity (current) of the stimulus signal output to the electrode member 3, thus making it possible to prevent or alleviate apnea and infrequent respiration. In that case, the information from the respiratory detection unit 26 contains a number of uncertainties depending on differences in personal disease condition and personal physical condition. Accordingly, although this information is taken as an auxiliary element when used, in this case, proposed is a respiratory abnormality improvement apparatus intended to apply to a living body an electric stimulus of an intensity ranging from 0% to 100% which is controlled by a timer built in the control CPU 21, regardless of synchronism or asynchronism with apnea and infrequent respiration.

The fundamental operation is as follows. That is, the electric stimulus is applied to a user as the first stimulus signal to such a degree as not to undermine the user's sleeping quality during sleep, for the purpose of preventing apnea and infrequent respiration. Further, when having taken in the information peculiar to apnea and infrequent respiration from the respiration detection unit 26, the second stimulus signal of a current level different from that of the first stimulus signal is applied to the user while enhancing the current level of the electric stimulus and changing the intensity thereof until the information is improved or for a certain period of time. With regard to the respiratory abnormality improvement apparatus of the present embodiment, the main body 1 includes the stimulus generating unit 51 capable of realizing the aforementioned operation.

As stated above, sensor information from the respiration detection unit 26 for detecting the respiratory condition of a patient is considered and used as an auxiliary information due to the problem of detection accuracy. Hence, the detection accuracy may be an approximate accuracy, and usually, it is preferred in terms of simplicity that a G (acceleration) sensor mounted on the main body 1 be used as the respiration detection unit 26 to capture a body motion of the patient and detect the respiratory abnormality from a change in the acceleration of the body motion. Further, as the respiration detection unit 26, when using a flow sensor utilizing a pressure sensor, the respiratory abnormality can be detected with a considerable accuracy. However, it causes degradation in tolerability to attach a cannula near a nasal cavity every night.

While the respiration detection unit 26 capable of sensing a sound of a patient is also desirable, it is hard to determine whether or not the respiratory abnormality is occurring, due to a mixture of other sounds and a variety of snoring types. While the respiration detection unit 26 capable of detecting a blood oxygen saturation level of the patient can be a desirable sensor, it degrades the tolerability of the patient due to a delay in response of several tens of seconds and the fact that sensors are to be attached to a finger and a earlobe. In addition, while there exists a respiration detection unit 26 capable of sensing brain waves and electrocardiographic waveforms, it is difficult to, for example, attach and set up electrodes. In any case, all sensors that can detect the respiratory abnormality of the patient are available as the respiration detection unit 26.

Figure 2:
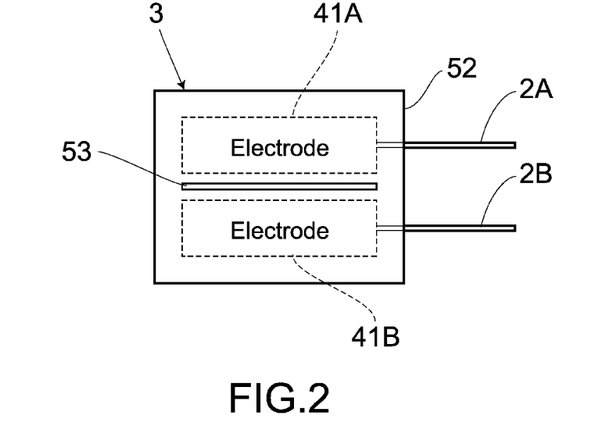
FIG. 2 is a plain view of a main part illustrating one example of cords and an electrode member in the present invention.
Figure 3:
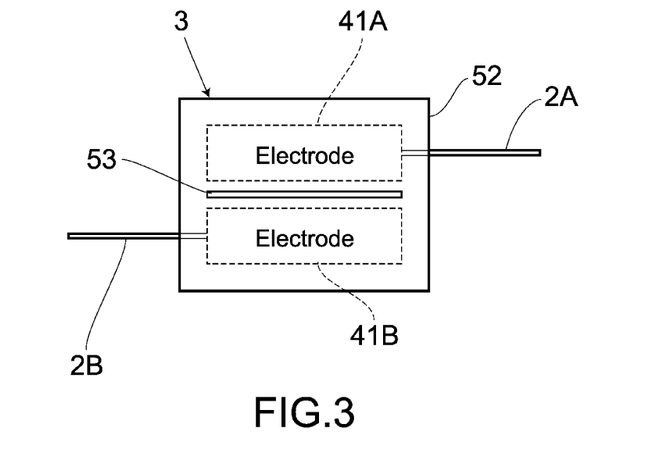
FIG. 3 is a plain view of a main part illustrating a different example of the cords and the electrode member in the present invention.

Next is a detailed description of structures of the cords 2A, 2B and the electrode member 3 with reference to FIG. 2 and FIG. 3.

In these figures, numerical symbols 41A, 41B denote the above electrodes as a pair of output terminals. Each of the electrodes 41A, 41B is electrically connected to the stimulus generating unit 51 inside the main body 1 through a pair of flexible cords 2A, 2B for connection. A numerical symbol 52 denotes a cover member for parallel holding the electrodes 41A, 41B that are rectangular in planar view. This cover member 52 is made of a flexibility- and adhesion-rich material such that it can be detachably attached to a mental region of the patient. The cover member 52 referred to here is employed also for reinforcing an adhesion of and protecting the electrode member 3 used in the apparatus. Particularly, since the cover member 52 with an adherence property has an appropriate moisture permeability (aeration property), an uncomfortable feeling such as a sweaty or itchy feeling can be reduced when the cover member 52 is attached to the affected area. Conversely, if the cover member 52 is not breathable, a steamed and sweaty condition due to perspiration makes it easy for the cover member 52 to be peeled off the affected area.

In the present embodiment, in order to provide a respiratory abnormality improvement apparatus that is, regardless of gender, targeted at children and adults, an unwoven cloth superior in stretchability is desirably employed as the planar cover member 52 of the electrode member 3. The reason is that patients suffering from the sleep apnea syndrome are not only adults but children in large numbers, and a present situation is that children imperfect in skeletal formation are unsuited to employ an nCPAP (Nasal Continuous Positive Airway Pressure). However, the cover member 52 only flexible in all directions gives rise to "buckling" of the electrodes 4A, 4B to allow both the electrodes 41A, 41B to come into contact with each other, thus generating an abnormal current (due to a short circuit). Therefore, in the present embodiment, in order to avoid such a phenomenon, the unwoven cloth is regulated in formation so as to be provided with flexibility in a vertical (perpendicular) direction and non-flexibility in a lateral (horizontal) direction. In addition, it is a planar cloth to be generally employed as a taping. By employing the unwoven cloth as the cover member 52, however, the ventilation is improved and an effect for preventing perspiration or the like is also obtained.

The cover member 52 is formed with a slit 53 serving as a vent that allows a surface exposed outside and a surface attached to the affected area to be communicated with each other. This slit 53 is formed between a pair of the electrodes 41A, 41B arranged side by side in a planar manner. Instead of the slit 53, an incision may be formed in the cover member 52 as the vent. In addition, a shape of the vent may be arbitrarily changed depending on a shape and size of the electrodes 41A, 41B. In the present embodiment, the incision and the slit are formed in the adhesive cover member 52 employed for the electrode member 3, whereby the uncomfortable feeling at the time of attaching the electrode member 3 to the affected area can be further reduced while considering such advantages that the electrode member 3 is easily subjected to three-dimensional bend, the steamed and sweaty condition can be eliminated and the electrode member 3 can be easily peeled off after use.

In FIG. 2 and FIG. 3, a cord 2A connected to one electrode 41A and a cord 2B connected to the other electrode 41B, differ from each other in a direction by which they are drawn out. Specifically, although the cords 2A, 2B shown in FIG. 2 are respectively drawn from the same side of the paired electrodes 41A, 41B, the cords 2A, 2B shown in FIG. 3 are respectively drawn from different sides of the electrodes 41A, 41B. Particularly in FIG. 3, with the electrodes 41A, 41B centered, one cord 2B is drawn in a direction opposite to, or at 180 degrees to, the drawing direction of the other cord 2A. The cord 2B, however, may be drawn in a direction at 90 degrees or other degrees to the drawn direction of the other cord 2A. As a result, tensile forces arising from the cords 2A, 2B are applied separately to the different sides of the electrodes 41A, 41B, eventually the different sides of the electrode member 3, thus preventing the electrode member 3 from being peeled off due to the tensile forces of the cords 2A, 2B.

Next is a description of the behavior of the above configuration based on the waveforms shown in FIG. 4 to FIG. 7. In these figures, with time indicated on an abscissa axis, a level change of the stimulus current corresponding to the output current is graphed as if a level meter value is expressed. Accordingly, an actual stimulus current waveform is composed of an aggregate of fine electric pulses shown in these figures and those existing also in the lower side (minus side) in the form of a similar figure.

When using the present apparatus, the electrode member 3 is attached to the mental region of a patient in advance by utilizing the adhesion of the cover member 52. At this time, in order to give a directionality for the attachment of the electrode member 3, the cover member 52 is formed into a horizontally long shape, and therefore a portion of the cover member 52 in the longitudinal direction is inevitably attached to a portion of the mental region in a left-right direction. In this way, the electrodes 41A, 41B are aligned on a portion of the mental region in an anterior-posterior direction.

When completing the attachment of the electrode member 3 to the patient in this way, by pressing a switch of the input unit 25, an output start of the stimulus signal is instructed to initiate therapy. As a result, the output amplitude control unit 22 receives the first control signal from the first control signal generating unit 43 to output a variable output signal in the range of DC 0V to 10V to the center tap of the primary winding 39 of the transformer 38, and the output pulse width control unit 28 receives the second control signal from the second control signal generating unit 44 to output a pulse output signal to the gate of one of the FETs 36, 37.

When applying the plus-side pulse output signal from the output pulse width control unit 28 to the gate of the FET 36, the FET 36 turns on during an on-pulse period of the plus-side pulse output signal to ground one end of the primary winding 39 (dotted side), thereby inducing a voltage on one end of the secondary winding 40 (a dotted side) in proportion to a voltage level of the variable output signal. Further, when applying the minus-side output signal to the gate of the FET 37 from the output pulse width control unit 28 with the variable output signal being output to the center tap of the primary winding 39 of the transformer 38, the FET 37 turns on during an on-pulse period of the minus-side pulse output signal to ground the other end of the primary winding 39 (a non-dotted side), thereby inducing a voltage on the other end of the secondary winding 40 (non-dotted side) in proportion to the voltage level of the variable output signal. Accordingly, as long as the voltage level of the variable output signal is not 0, the stimulus current composed of positive- or negative-polarity electric pulses depending on the voltage level of the variable output signal is applied to the electrodes 41A, 41B of the electrode member 3 from the stimulus generating unit 51.

When receiving an instruction signal for initiating an output of the stimulus signal from the input unit 25, the stimulus generating unit 51 imports a detection signal as needed from the respiration detection unit 26 to generate a first stimulus signal in the electrodes 41A, 41B of the electrode member 3 at a current level preset at a given clock time unless the respiration detection unit 26 senses the respiratory abnormality of the patient. In contrast, when the respiration detection unit 26 has sensed the respiratory abnormality of the patient, the stimulus generating unit 51 determines that the patient is subjected to the respiration abnormality, and thereby generates a second stimulus signal in the electrodes 41A, 41B of the electrode member 3 at a current level higher than that of the first stimulus signal.

Further, the stimulus generating unit 51 imports a monitored signal as needed from the electrode-member monitoring unit 27. When the electrode-member monitoring unit 27 has sensed such malfunction as the peeling of the electrode member 3, a short circuit, and wire breaking, the stimulus generating unit 51 lowers the current level of the stimulus signal to, e.g., a level slightly lower than a preset one. Then, when the malfunction is no longer sensed, the stimulus generating unit 51 returns the stimulus signal to the originally preset current level. Further, when electrode-member monitoring unit 27 has sensed a condition where the current flowing through the electrode member 3 had decreased or the voltage applied to the electrode member 3 had risen such that a resistant value of the electrode member 3 including the cords 2A, 2B had considerably increased, electrode-member monitoring unit 27 may allow an annunciation unit not shown to output a warming sound to stop the output operation of the stimulus signal. As a result, various anxieties attributable to the malfunction of the conductor unit 3 can be cast aside.

In the present embodiment, the sensor of the respiration detection unit 26 is utilized in an auxiliary manner. However, in consideration of the problem of detection accuracy of the sensor, however, the fundamental stimulus action for insuring safety is carried out by applying the first stimulus signal from the electrode member 3 to the patient at the initiative of a timer. This first stimulus signal prevents or alleviates apnea and infrequent respiration of the patient. Specifically, the generation timing of the first stimulus signal is controlled by the timer incorporated in the control CPU 21. The fundamental stimulus action of the present apparatus, however, does not require he synchronism and asynchronism with apnea and infrequent respiration. When the respiration detection unit 26 has detected the respiration abnormality such as apnea and infrequent respiration, a stimulus action stronger than the fundamental stimulus action is only applied as the second stimulus signal.

Figure 4:
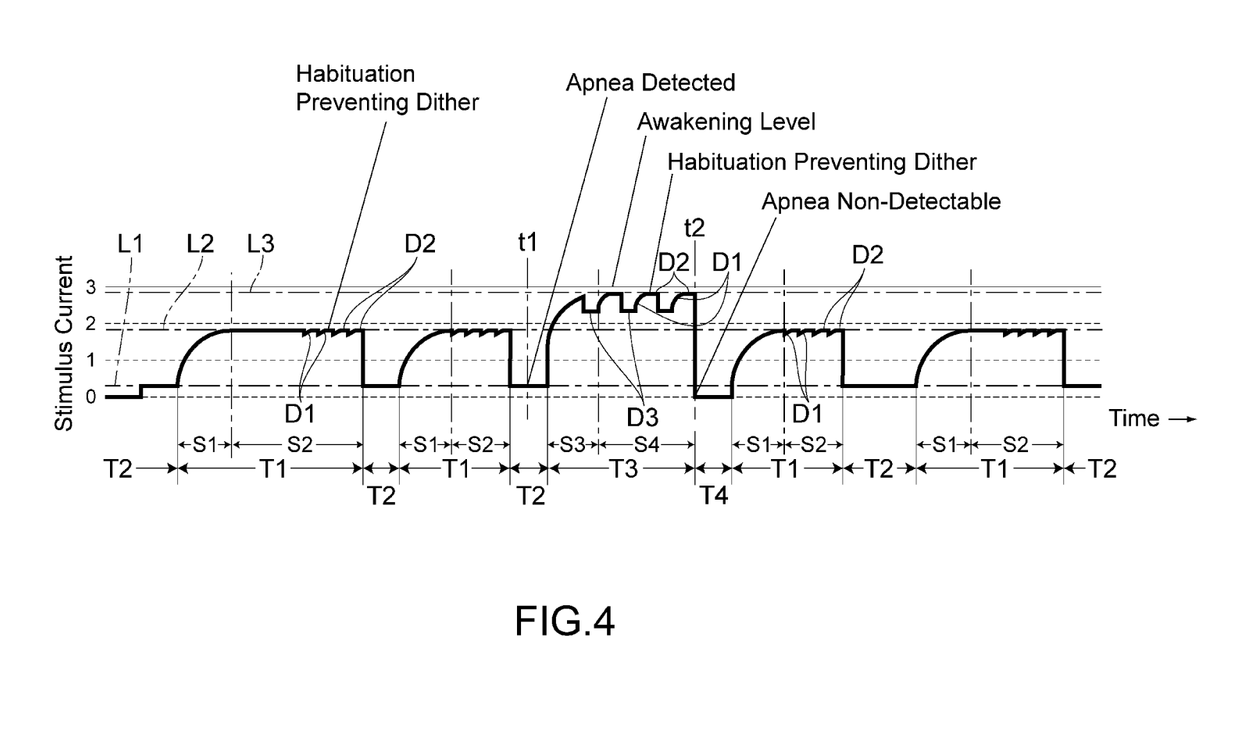
FIG. 4 is an example of a first waveform of a stimulus current output from a stimulus generating unit in the present invention.

FIG. 4 shows an example of a waveform after a given period of time has elapsed from an output start of the stimulus signal. In FIG. 4, T1 denotes a conduction period of the first stimulus signal, T2 denotes a break period of the first stimulus signal, T3 denotes a conduction period of the second stimulus signal, and T4 denotes a break period of the second stimulus signal. Although not shown in FIG. 4, the stimulus generating unit 51 generates the stimulus signal in such a manner that the initiation of therapy starts from a 0 level of the stimulus current, in other words, the voltage of the variable output signal starts from 0V, and once an output to the electrode member 3 starts, a pattern is then formed so that most level of the stimulus current subsequent to the start does not drop to 0. When desiring to change stimulus feeling of the patient, however, a pattern in which the stimulus current drops to 0 by means of the stimulus generating unit 51 may be combined. In an example of a waveform shown in FIG. 4, immediately after the respiration detection unit 26 detects no apnea any more, the level of the stimulus current is dropped to 0 during the break period T4 of the second stimulus signal for the purpose of changing the stimulus feeling.

The stimulus generating unit 51 in the present embodiment determines operation timings of all the stimulus signals essentially based on one timer. These timings include, e.g., timing of fluctuating the stimulus current (e.g., "a dither for preventing habituation" shown in FIG. 4), intervals (the break periods T2, T4 in which the level of the stimulus current is allowed to drop to 0 or the first level L1 that is near 0, and the conduction periods T1, T3 corresponding to stimulus periods during which a given stimulus is being applied to a patient), and an entire conduction period.

The level of the stimulus current of the first stimulus signal is set so as to be up to a level lower than an arousal limitation level at which the patient awakes. The stimulus generating unit 51 may be configured so as to be able to change this preset value by the instruction signal from the input unit 25. The stimulus generating unit 51 continues to apply the first stimulus signal at an output current level not higher than the arousal limitation level from the start of therapy, and thereby the respiratory abnormality such as apnea and infrequent respiration can be prevented or alleviated without applying an electric stimulus of a current level higher than necessary during the therapy and awakening the patient.

A maximum value of the level of the stimulus current during the conduction period T1 of the first stimulus signal that is periodically generated, increases over time. Specifically, immediately after an output start of the first stimulus signal, that is, immediately after the patient has gone to bed, the level of the stimulus current during the conduction period T1 of the first stimulus signal is so low that the patient can barely perceive, and thereafter as time advances, the patient falls asleep, the level of the stimulus current during the conduction period T1 of the first stimulus signal increases to a value suitable for therapy.

However, since the time required for the patient to fall asleep varies vastly from person to person, it is preferred that a length of time during which the level of the stimulus current increases from the output start of the first stimulus signal to a value of the stimulus current suitable for therapy be arbitrarily changed through an operation to the input unit 25. Further, as another modification, during the aforementioned length of time, a rate of increasing the level of the stimulus current may be inconstant and increased with time. As a result, for a little while from the output start of the first stimulus signal, the level of the stimulus current during the conduction period T1 is not increased significantly, thereby enabling the patient to fall asleep while being less affected by the stimulus signal. Then, as shown in FIG. 4 to FIG. 7, when the above length of time has elapsed from the start of therapy, the maximum value of the level of the stimulus current during the conduction period T1 of the first stimulus signal is fixed at a constant level (i.e. a second level L2).

Thus, when the respiration detection unit 26 has detected the apnea of the patient at the time t1 with the first stimulus signal being applied to the patient by the stimulus generating unit 51, and after the break period T2 of the first stimulus signal has elapsed, the second stimulus signal whose maximum stimulus current level is higher than that during the conduction period T1 of the first stimulus signal is output to the electrode member 3 during the conduction period T3. In FIG. 4 to FIG. 7, this is shown as a third level L3 during the conduction period T3 that is higher than the second level L2 during the conduction period T1. In the present embodiment, even when the respiration detection unit 26 has detected the respiratory abnormality such as apnea and infrequent respiration to increase its output to the second stimulus signal, a less strong stimulus current (the first stimulus current) is applied in advance to cause a patient's body to become habituated to the stimulus current, hence a pain and the uncomfortable feeling is minimized, and a stimulus current higher than a current suddenly applied can be applied.

In the example of a waveform shown in FIG. 4, the level of the stimulus current during the conduction period T3 of the second stimulus signal that increases at the time of developing the respiratory abnormality, is set within a range lower than the arousal limitation level where awakening does not occur even at a maximum level (i.e. the third level L3 is lower than the arousal limitation level). However, when apnea and infrequent respiration are not improved even with such a stimulus being applied for a certain period of time, it is possible to set a further higher current level shown in FIG. 5 as an other waveform example, in order to avoid danger (see a fourth level L4 during a conduction period T3' of the second stimulus signal). In addition, in this case, in order to prompt the patient to awake, an output intended to awaken the patient is applied.

Further, in the example of the waveform shown in FIG. 4, until the respiration detection unit 26 no longer detects apnea of the patient at a time t2, continuously output to the electrode member 3 during the conduction period T3 is the second stimulus signal whose stimulus current level has been increased to a level higher than that during the conduction period T1 of the first stimulus signal. Accordingly, the duration of the conduction period T3 depends on the detected result coming from the respiration detection unit 26. On the other hand, in an example of a waveform shown in FIG. 5, in spite of the detected result from the respiration detection unit 26, the conduction period T3 of the second stimulus signal exhibits a constant length. And, during the break period T4 thereafter, when the respiration detection unit 26 has detected the apnea of the patient, the second stimulus signal makes the transition from the break period T4 again to the conduction period T3. Nonetheless, if the respiration detection unit 26 continues to detect the apnea of the patient, the stimulus current level of the second stimulus signal of the next conduction period T3' is set higher than the arousal limitation level. Thus, until the apnea of the patient becomes undetectable by the respiration detection unit 26 at the time t2, the second stimulus signal whose stimulus current level output has been increased is repeatedly applied to the patient during the conduction periods T3, T3'. In this fashion, when the respiration abnormality has occurred, the stimulus generating unit 51 continues to apply from the electrode member 3 to the patient's living body the second stimulus signal of a stimulus current level different from that of the first stimulus signal, until the abnormality becomes improved, thereby effectively improving the respiration abnormality of the patient during sleep.

Figure 5:
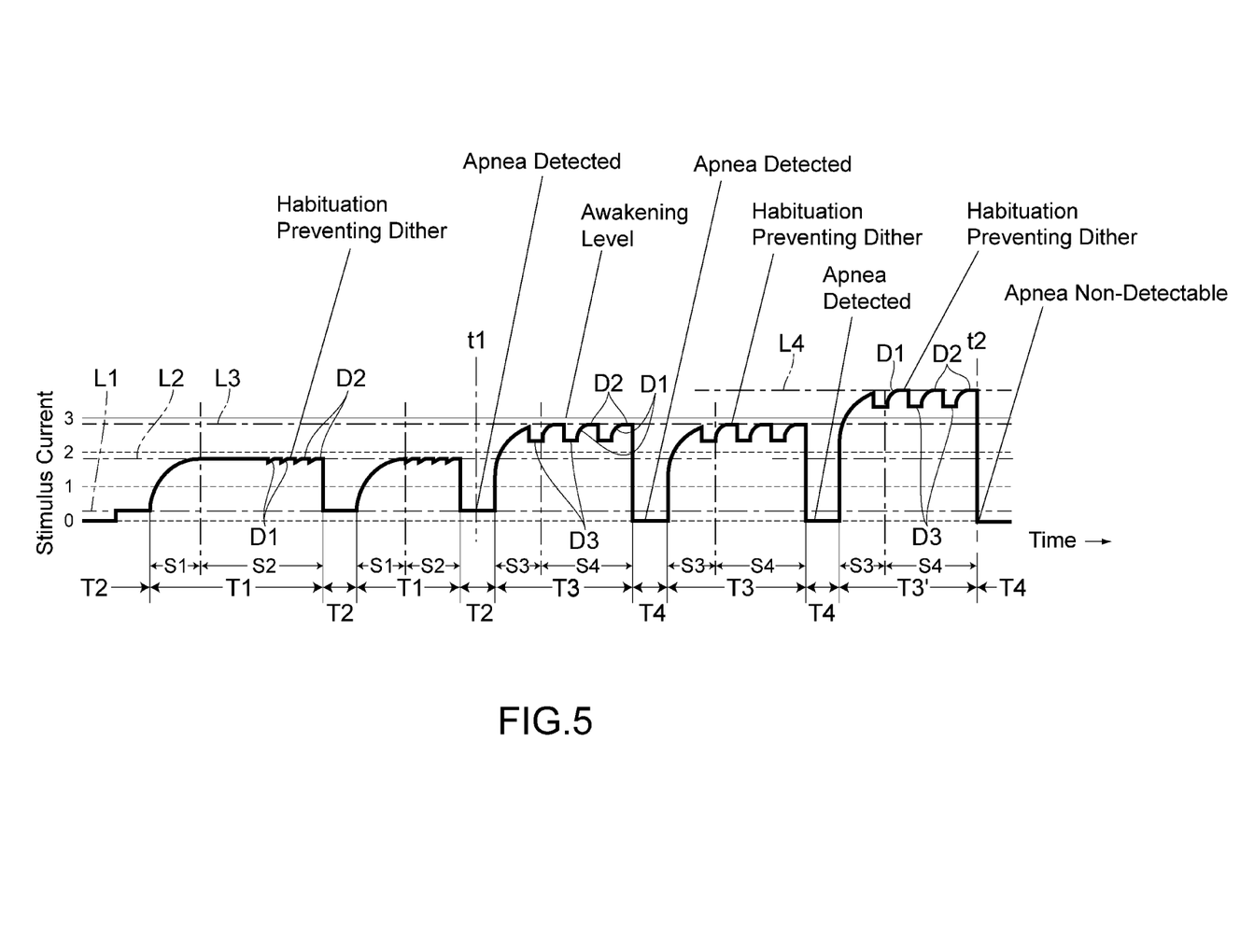
FIG. 5 is an example of a second waveform of the stimulus current output from the stimulus generating unit in the present invention.

During the output of the stimulus signal, provided are the break periods T2, T4 for appropriately decreasing the stimulus current from 0 to a level that causes no muscle tension (the first level L1 of 0.5 to 1 in FIG. 4 and FIG. 5). These break periods T2, T4 are intended to prevent intramuscular lactic acid attributable to fatigue from occurring; and torpor resulting from continuous muscle tension. Further, by decreasing the first level L1 equivalent to the maximum stimulus current level during the break period T2 to a few percentage or lower of the second level L2 equivalent to the maximum stimulus current level during the conduction period T1; or of the third level L3 equivalent to the maximum stimulus current level during the conduction period T3, the feeling of stimulation on the patient becomes almost imperceptible. However, the habituation of stimulus caused by the electric conduction can be expected, and therefore a pain caused by a large electric stimulus during the next conduction periods T1, T3 can be alleviated.

Particularly, during the break period T2 of the first stimulus signal, such a stimulus current that the basic application thereof is imperceptible is applied to the patient. Even during this period, however, the stimulus current is applied and hence there are provided such advantages that a skin becomes habituated to electricity and an attached state of the electrode member 3 can be learnt from a current and a voltage by the conductor unit monitoring means 27. Further, during the break period T4 of the second stimulus signal, the level of the stimulus current becomes 0 and thereby the strong muscle tension due to the second stimulus signal applied during the last conduction period T3 can be effectively alleviated by the break period T4.

The stimulus generating unit 51 interposes the break periods T2, T4 in which the level of the stimulus current of the first stimulus signal is automatically (using a program) decreased by the timer. The lengths of the break periods are not fixed and the stimulus generating unit 51 changes the lengths of the conduction periods T1, T3 and break periods T2, T4 at the time of falling asleep and during other periods and further at undulating time intervals (1/f), thereby preventing a sleeping quality from degrading as much as possible. The stimulus generating unit 51 may be configured in a manner such that these settings of the time lengths can be varied by the instruction signal from the input unit 25.

Further, the stimulus generating unit 51 generates and outputs the stimulus signal so as to gradually slack the rising of the level of the stimulus current over time when the conduction periods T1, T3 rise. This is because if the level of the stimulus current rapidly rises during the conduction periods T1, T3, a strong pain is generated (a human body is similar to a capacitor and hence when a current rapidly rises, a differential current becomes larger to cause a stimulus to be stronger in proportion to the magnitude of the differential current). As for the rise and fall of the conduction periods T1, T3, a change of the level of the stimulus current with respect to time is set as forms of a straight-line type, a logarithmic-curve type, and an inverted logarithmic-curve type, thereby changing the way a stimulus is felt. Therefore, a plurality of patterns are prepared preliminarily in the stimulus generating unit 51 to select a desirable pattern from these patterns and then an output level of the stimulus signal may be allowed to vary using the desirable pattern at the time of the rise and fall of each of the conduction periods T1, T3.

Shown in FIG. 4 to FIG. 7 are a first interval S1 and a second interval S2 in the conduction period T1. Particularly, the first interval S1 is an interval where the stimulus current level rises from 0 or the first level L1 and reaches the maximum second level L2. The second interval S2 follows the first interval S1, and is an interval where the stimulus current level is maintained at the maximum second level L2 before making the transition to the next break period T2. Also shown in FIG. 4 to FIG. 7 are a first interval S3 and a second interval S4 in the conduction period T3. Particularly, the first interval S3 is an interval where the stimulus current level rises from 0 or the first level L1 and reaches the maximum third level L3 or fourth level L4. The second interval S4 follows the first interval S3, and is an interval where the stimulus current level is maintained at the maximum third level L3 or fourth level L4 before making the transition to the next break period T4.

And now, a human body becomes habituated to an unchanged current of an electric stimulus to cause cutaneous feeling and a muscle to become paralyzed and allow a human body's reaction to petrify. When a stronger stimulus is needed in a conventional method, there is no alternative other than to further increase the stimulus current, which results in various concerns responsible to an excessive current. Therefore, in the present embodiment, in order to prevent these concerns, a stimulus intensity is increased not only by merely heightening the level of the stimulus current but by cumulatively increasing the level of the stimulus current while repeatedly heightening and lowering the level of the stimulus current and further repeating an increase and decrease of the stimulus current even during a continuous stimulus application period in which the amplitude of the electric pulses continuously generated is kept constant. In this way, in order to apply an effective stimulus even with a low current, the stimulus generating unit 51 inserts the dither during the conduction periods T1, T3 of the stimulus signal to prevent the human body from becoming habituated. During each of these conduction periods T1, T3, there exist the second intervals S2, S4 in which a current amplitude becomes constant after the first intervals S1, S3 in which an electric amplitude of the electric pulse continuously generated alternatively in positive and negative polarities gently rises. However, a duration of a constant level of the same waveform weakens the feeling of stimulus (the feeling becomes paralyzed). Hence, without varying an average current when needing a constant stimulus within the conduction periods T1, T3, the dither for increasing and decreasing a current acting as an output level of the stimulus signal within a short period of time (normally within 0.1 second) is inserted during a given period of time, thereby holding the feeling of stimulus applied to the patient constant.

Further, even when applying a predetermined stimulus intensity (the level of the stimulus current), the dither as in the present embodiment is added to repeatedly contract and relax the affected area by little and little, and thereby a muscular movement is smoothed, thus permitting the respiratory abnormalities such as apnea and infrequent respiration to be prevented and improved. For example, this technique is derived from the one employed to smooth initial motions of a hydraulic cylinder and solenoid mechanism of a heavy machine, and then the same is equally true of an initial motion of a human body (muscle) since large force is required for the initial motion of the human body.

In addition, in examples of the waveforms shown in FIG. 4, FIG. 5, there is provided a level rising period D1 in which a rising at the time of the ascending of the level of the stimulus current is allowed to be gradual during a dither insertion period so that the patient is prevented from feeling a stimulus stronger than necessary. The level of the stimulus current, however, may be allowed to rapidly vary to further enhance the feeling of stimulus to the patient. The dither referred to here is realized by varying A/D (analogue/digital) values from a control CPU 21 and the wave producing CPU 32 by little and little.

As shown in FIG. 4 and FIG. 5, as for the conduction period T1 at the time of generating the first stimulus signal, the dither is inserted not into the first interval S1, but only into the second interval S2. During such dither insertion period in the conduction period T1, repeated are the level rising period D1 and a level upper-limit period D2. Particularly, the level rising period D1 is a period where the stimulus current level rises from the lower limit to the upper limit. The level upper-limit period D2 follows the level rising period D1, and is a period where the stimulus current level is maintained at an upper limit identical to that of the second level L2 for a certain period of time. When a transition is made from the level upper-limit period D2 to the level rising period D1, the stimulus current level changes from the upper limit to the lower limit.

In contrast, as for the conduction period T3 at the time of generating the second stimulus signal, the dither is continuously inserted in all the first interval S3 through the second interval S4. During the dither insertion period in the conduction period T3, repeated are the level rising period D1, the level upper-limit period D2 and a level lower-limit period D3. Here, the level upper-limit period D2 follows the level rising period D1, and is a period where the stimulus current level is maintained at an upper limit identical to that of the third level L3 and the fourth level L4 for a certain period of time. The level lower-limit period D3 follows the level upper-limit period D2, and is a period where the stimulus current level is maintained at a lower limit lower than that of the third level L3 and the fourth level L4 for a certain period of time. That is, the level lower-limit period D3 is provided only in the conduction period T3 at the time of generating the second stimulus signal, but not in the conduction period T1 at the time of generating the first stimulus signal.

The dithers shown in FIG. 4, FIG. 5 increase and decrease the level of the stimulus current of the first stimulus signal during the conduction period T1 and the level of the stimulus current of the second stimulus signal during the conduction period T3. The feeling of stimulus, however, varies by an increase and decrease in frequency and hence the same effect can be obtained by inserting the dither produced by varying frequency.

Figure 6:
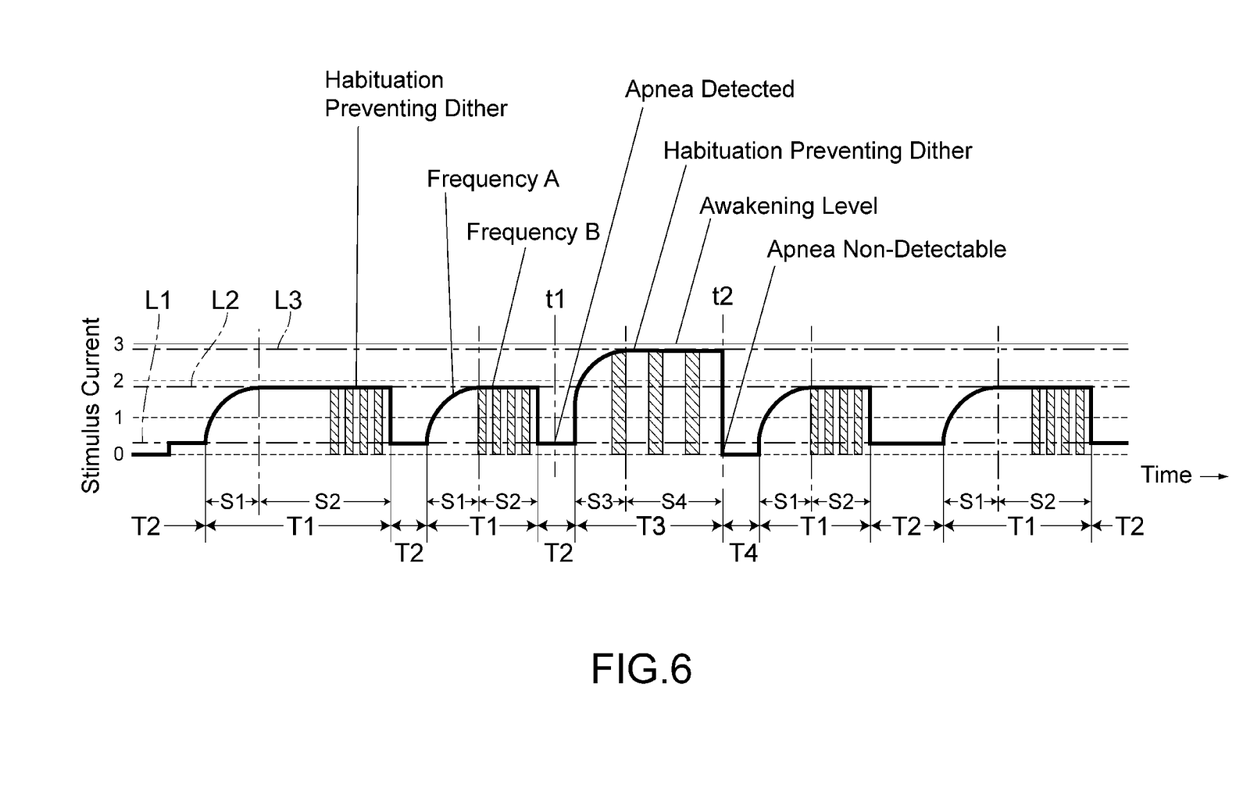
FIG. 6 is an example of a third waveform of the stimulus current output from the stimulus generating unit in the present invention.

FIG. 6 shows an example of a waveform produced by inserting the dither, in which a frequency of a stimulus signal is varied, into the conduction periods T1, T3. The stimulus generating unit 51 outputs, to the electrode member 3, a stimulus signal whose frequency is kept constant in a solid-line region shown as "frequency A" and varies bit by bit in a shaded region shown as "frequency B"

Figure 7:
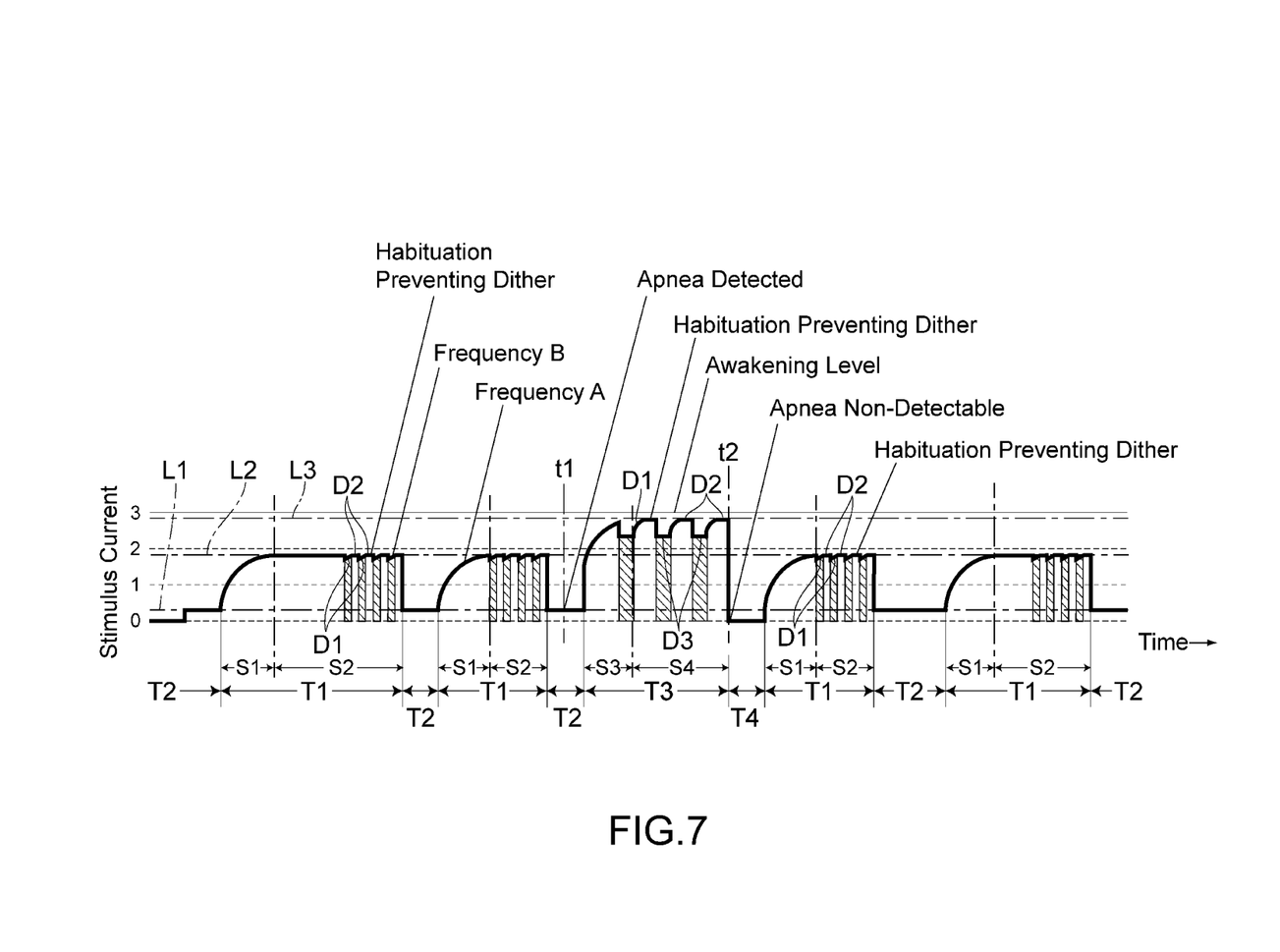
FIG. 7 is an example of a fourth waveform of the stimulus current output from the stimulus generating unit in the present invention.

Further, as shown in an example of a waveform in FIG. 7, the dither in which both a current level and frequency of the stimulus signal are varied may be inserted into the conduction periods T1, T3. In this case, the stimulus generating unit 51 outputs, to the electrode member 3, such a stimulus signal whose frequency is kept constant in a solid-line region shown as "frequency A" but varies in a shaded region shown as "frequency B".

In addition, in the example of each waveform shown in FIG. 4 to FIG. 7, the dither for preventing habituation may be inserted during a period in which the level of the stimulus current at initial stages of the conduction periods T1, T3 increases, Variations in current and frequency during the dither does not need to be constantly repeated, but may be freely set in accordance with a needed stimulus pattern. Further, the variations in current and frequency may be not synchronized with the patient's respiration detected by the respiration detection unit 26.

Especially, when focusing on a "frequency B," as for the conduction period T1, the frequency of the first stimulus signal is repeatedly increased and decreased only during the level rising period D1 in the dither insertion period. In contrast, as for the conduction period T3, the frequency of the second stimulus signal is repeatedly increased and decreased only during the level lower-limit period D3 in the dither insertion period.

When the patient has awakened during therapy, by operating the input unit 25 to instruct to stop outputting the stimulus signal, a variable output signal from the output amplitude control unit 22 and the pulse output signal from the output pulse width control unit 28 rapidly stop their own outputs and then the output of the stimulus signal to the mental region of the patient is cut off immediately. Consequently, the patient can cut off the uncomfortable feeling caused by the stimulus signal that keeps being applied to the wakeful patient. Further, when sleeping afterward, only by performing the pressing operation on the input unit 25, it is possible to instruct an output start of the stimulus signal to the control CPU 21. In addition, since a strong stimulus signal is not applied immediately after falling asleep, an adverse effect on sleep due to this stimulus signal can be eliminated.

Besides, although not shown, not only the conduction periods T1, T3, T3' and the break periods T2, T4 but a time setting of the dither for preventing the habituation are allowed to become arbitrarily variable from the outside by the input unit 25, thereby enabling a more effective therapeutic effect to be obtained. Furthermore, this scheme can be simply realized only by changing a control program within the control CPU 21.

As a desirable method to use the present apparatus, fatness of a neck is dissolved or improved and muscles in a conduction portion are toned up, and thereby a condition hard to cause the apnea can be created by applying a prolonged electric stimulus to a human body everyday. Age-related muscular weakening and an accumulation of fat due to obesity are a frequent cause of the sleep apnea syndrome. On the other hand, a long-period electric stimulus is, as is verified by an EMS device, likely to tone up muscles and reduce fat. One cause of such a sleep apnea syndrome is eliminated through a periodical use of the present apparatus, and thereby even when interrupting the same therapy after a specific period of time, an effect can be expected to be maintained. Specifically, by employing the apparatus of the present embodiment in accordance with the method for using the same, a mental region muscle and muscles near the mental region are inevitably toned up during user's (patient's) sleep every night, and further the apparatus is employed everyday to continuously repeat an exercise (EMS) brought about by the electric stimulus, thereby permitting also a slimming effect to be expected eventually.

As described above, in the present embodiment, there is provided the respiratory abnormality improvement apparatus for applying the stimulus signal generated in the stimulus generating unit 51 to the patient as the electric stimulus. The respiratory abnormality improvement apparatus includes the respiration detection unit 26 with the sensor acting as a detection unit for detecting the respiratory condition of the patient and the stimulus generating unit 51, which is configured so as to generate, as the stimulus signal applied to the electrode member 3 attached to the patient, the first stimulus signal at the level of the current preset at a predetermined clock time and the second stimulus signal whose current level differs from that of the first stimulus signal when the patient is judged to be under the condition of respiratory abnormality based on the detection signal from the respiration detection unit 26.

In this case, by applying, from the stimulus generating unit 51, as the first stimulus signal the electric stimulus at such a current level as not to debase the sleeping quality of the patient and thereby without applying the electric stimulus at the level of the current higher than necessary and awakening the patient, the respiration abnormality such as apnea and infrequent respiration can be prevented or alleviated. Further, when the detection signal peculiar to apnea and infrequent respiration is output with the first stimulus signal being applied to the patient, such a different second stimulus signal as to enhance the current level of the electric stimulus or vary the intensity of the level of the current is applied to the patient until such a peculiar detection signal is no longer present or for a specified period of time. In this fashion, when the respiratory abnormality has occurred, the second stimulus signal of a current level different from that of the first stimulus signal is applied as an appropriate electric stimulus until the respiratory abnormality is improved, thereby permitting the respiration abnormality of the patient during sleep to be effectively improved.

In addition, the stimulus generating unit 51 is configured as follows. That is, as for each of the first and second stimulus signals, repeated are the conduction periods T1, T3 where an electric pulse group having a current level greater than the first level L1 as a given level is generated; and the break periods T2, T4 where an electric pulse group having a current level not higher than the first level L1 is generated or where no electric pulse group is generated at all. Moreover, as for each conduction period T1, there exist the first interval S1 where the current level of the stimulus signal rises in a manner such that the rate of increase becomes gradually moderate with time; and the second interval S2 that follows the first interval S1 and where the current level of the stimulus signal becomes constant (Likewise, the first interval S3 and the second interval S4 exist in each conduction period T3).

Therefore, at the time of the rising of the conduction periods T1, T3, since generated and outputted is a stimulus signal whose increasing rate of stimulus current level gradually becomes moderate with time, a strong pain due to a rapid rising of the stimulus current level can be prevented from occurring.

Further, in the present embodiment, the stimulus generation unit 51 is configured so that a stimulus break period for lowering the current level to a level ranging from 0 to a level that causes no muscle tension of the patient is formed as the break period T2 of the first stimulus signal and the break period T4 of the second stimulus signal.

In this case, there are provided the stimulus break periods T2, T4 for appropriately lowering the current level to a level ranging from 0 to a level that causes no muscle tension during the conduction periods T1, T3 in which the stimulus signal is being applied to the patient. Consequently, the generation of lactic acid inside muscles resulting from fatigue and torpor due to continuous muscle tension can both be prevented. Further, when the current level during the break periods T2, T4 is lowered to a few percentage or lower of the current level of the stimulus signal that has been applied up to that time, regardless of the fact that the feeling of stimulus of the patient becomes almost imperceptible, the habituation of the electric stimulus due to electric conduction can be expected. Therefore, a pain attributable to the next large electric stimulus can be alleviated.

Further, in the present embodiment, the stimulus generating unit 51 is configured in a manner such that while the current level of the electric pulse group is maintained at the first level L1 as a given level other than 0 during the break period T2 at the time of generating the first stimulus signal, the current level of the current pulse group is 0 during the break period T4 at the time of generating the second stimulus signal.

In this case, a living body can be habituated to an electric current when subjected to a small amount of electric current. Further, the stimulus current level becomes 0 during the break period T4 of the second stimulus signal, thereby effectively alleviating, in the break period T4, a strong muscle tension caused by the second stimulus signal that has been applied during the conduction period T3 until then. Furthermore, after apnea is no longer detected by the respiratory detection unit 26, the level of the stimulus current is dropped to 0 during the break period T4, thus effectively changing the feeling of stimulation caused to the patient.

Furthermore, in the present embodiment, the stimulus generating unit 51 is so configured that during the conduction periods T1, T3 of the stimulus signal which generates a current level higher than the first level L1, during the first intervals S1, S3 of an increase in the current level of the stimulus signal or during the second intervals S2, S4 as certain periods after the increase, inserted is the dither in which the current level of the stimulus signal repeats an increase and a decrease.

In this case, during the conduction periods T1, T3 of the stimulus signal, when attempting to boost the stimulus intensity during the first intervals S1, S3, the current level of stimulus signal is not simply increased but the current level is raised while increasing and decreasing the current level repeatedly and repeating the increase and decrease of the current level even during the continuous periods i.e. the second intervals S2, S4 for keeping the following current level constant, thereby making it possible to apply an effective stimulus even with a low current. That is, when applying the stimulus signal in such a manner as to solely increase the stimulus signal with the same waveform unchanged or as to be applied continuously at the constant current level, the feeling of stimulus weakens to paralyze human body's sense. Hence, when needing a constant stimulus during these conduction periods T1, T3, the dither for increasing and decreasing the current level in a short amount of time (usually within 0.1 sec) is inserted without changing an average current, thereby enabling the feeling of stimulus to be kept constant.

Moreover, in the present embodiment, the stimulus generating unit 51 is so configured that during the conduction periods T1, T3 of the stimulus signal, the dither is inserted to repeat an increase and a decrease in a frequency of the stimulus signal during the first intervals S1, S3 of an increase in the current level of the stimulus signal or during the certain periods i.e. the second intervals S2, S4 after the increase.

In this case, during the conduction periods T1, T3 of the stimulus signal, when raising the stimulus intensity during the first intervals S1, S3, the current level of the stimulus signal is not simply increased but the current level is raised while increasing and decreasing the frequency repeatedly and repeating the increase and decrease of the frequency even during the following continuous periods i.e. the second intervals S2, S4 for keeping the current level constant, thereby making it possible to apply an effective stimulus even with a low current. That is, when applying the stimulus signal in such a manner as to solely increase the stimulus signal with the same waveform unchanged or as to be applied continuously at the constant current level, the feeling of stimulus weakens to paralyze human body's sense. Hence, when needing a constant stimulus within these conduction periods T1, T3, the dither for increasing and decreasing the frequency in a short amount of time is inserted, thereby enabling the feeling of stimulus to be kept constant.

Besides, in the present embodiment, the stimulus generating unit 51 may also be configured in a manner such that during the conduction periods T1, T3 of the stimulus signal, the dither is inserted to repeat an increase and a decrease in the current level and frequency of the stimulus signal during the first intervals S1, S3 of an increase in the current level of the stimulus signal or during the certain periods i.e. the second intervals S2, S4 after the increase.

In this case, during the conduction periods T1, T3 of the stimulus signal, when raising the stimulus intensity during the first intervals S1, S3, the current level of the stimulus signal is not simply increased but the current level is raised while increasing and decreasing both the current level and frequency repeatedly, and even during the following continuous periods i.e. the second intervals S2, S4 for keeping the current level constant, the current level and frequency are repeatedly increased and decreased, thereby making it possible to apply an effective stimulus even with a low current. That is, when applying the stimulus signal in such a manner as to solely increase the stimulus signal with the same waveform unchanged or as to be applied continuously at the constant current level, the feeling of stimulus weakens to paralyze human body's sense. Hence, when needing a constant stimulus within these conduction periods T1, T3, the dither for increasing and decreasing the current level and the frequency in a short amount of time is inserted, thereby enabling the feeling of stimulus to be kept constant.

Further, in the present embodiment, the stimulus generating unit 51 is configured as follows. That is, as for the conduction period T1 at the time of generating the first stimulus signal, the dither is not inserted into the first interval S1, but only inserted into the entire or a part of the second interval S2. Meanwhile, as for the conduction period T3 at the time of generating the second stimulus signal, the dither is continuously inserted from the midway of the first interval S3 through the entire second interval S4.

Due to the aforementioned configuration, when the patient is exhibiting no respiratory abnormality during the conduction period T1 of the first stimulus signal, the dither is to be inserted into the second interval S2 that is established after the stimulus current level has reached the second level L2 and thus stabilized, thereby making it possible to maintaining a constant feeling of stimulus without degrading the sleeping quality of the patient. Further, when it has been determined that the patient has exhibited a respiratory abnormality during the conduction period T3 of the second stimulus signal, the dither is to be inserted from the first interval S3 where the stimulus current level has not yet reached to the third level L3 and the fourth level L4, thereby preventing the feeling of stimulus caused to the patient from weakening at an early stage, thus making it possible to effectively prevent and improve respiratory abnormality.

Further, in the present embodiment, the stimulus generating unit 51 is configured in a manner such that during the dither insertion period of the conduction periods T1, T3, there is provided the level rising period D1 where the stimulus current level rises in a manner such that the rate of increase becomes gradually moderate with time.

Due to the aforementioned configuration, it is possible to prevent the patient from feeling a stimulus stronger than necessary, without impairing the effect brought about by inserting the dither into the conduction periods T1, T3.

As shown in FIG. 7, the stimulus generating unit 51 is configured in a manner such that during the dither insertion period of the conduction period T1 at the time of generating the first stimulus signal, the frequency of the stimulus signal repeatedly increases and decreases only during the level rising period D1 as a period where the stimulus current level rises.

Due to the aforementioned configuration, when the patient is exhibiting no respiratory abnormality, the frequency of the stimulus signal repeatedly increases and decreases only during the level rising period D1. For this reason, while the patient is prevented form feeling a stimulus stronger than necessary, a feeling of stimulus of a certain level can be obtained by changing the frequency of the stimulus signal, thereby preventing and improving the respiratory abnormality.

As shown in FIG. 7, the stimulus generating unit 51 is configured as follows. That is, during the dither insertion period at the time of generating the second stimulus signal, the frequency of the stimulus signal repeatedly increases and decreases only in the level lower-limit period D3 where the stimulus current level is maintained constant before rising.

Due to the aforementioned configuration, when it has been determined that the patient has exhibited a respiratory abnormality, the frequency of the stimulus signal repeatedly increases and decreases only during the level lower-limit period D3 prior to making the transition to the level rising period D1. For this reason, during the level rising period D1, while the patient is prevented from being subjected to a feeling of stimulus that is stronger than needed, a feeling of stimulus of a certain level can be effectively applied by changing the frequency of the stimulus signal, especially in an other level lower-limit period D3 where the stimulus current level is maintained at a lower limit.

Further, in the present embodiment, in order to output the stimulus signal to the patient, the apparatus includes the electrode member 3 attached to the patient and the electrode-member monitoring unit 27 for monitoring the current and the voltage which are applied to the electrode member 3.

In this case, due to an unconscious body motion of the patient during sleep, the electrode member 3 and the cords 2A, 2B connecting the electrode member 3 to the stimulus generating unit 51 are easily subjected to stress, and hence even if the electrode member 3 is firmly attached to the patient, in some cases the electrode member 3 may be peeled off in mid-course of therapy. Since such a partial conduction of the electrode member 3 causes a current to concentrate on the affected area, abnormal conditions such as the peeling of the electrode member 3, short circuit, and wire breaking are detected in a moment by the electrode-member monitoring unit 27, thereby allowing a concern resulting from the abnormality of the electrode member 3 to be prevented from occurring.

Furthermore, in the present embodiment, in order to output the stimulus signal to the patient, the present embodiment includes the electrode member 3 attached to the patient and the electrode-member monitoring unit 27 for monitoring a current and a voltage which are applied to the electrodes 41A, 41B of the electrode member 3 to detect the abnormality of the electrode member 3.

In this case, due to the unconscious body motion of the patient during sleep, the electrode member 3 and the cords 2A, 2B connecting the electrodes 41A, 41B of electrode member 3 to the stimulus generating unit 51 are apt to be subjected to stress, and hence even if the electrode member 3 is firmly attached to the patient, in some cases the electrode member 3 may be peeled off in mid-course of therapy. Since such a partial conduction of the electrode member 3 causes a current to concentrate on the affected area, abnormal conditions such as the peeling of the electrode member 3, short circuit, and wire breaking are detected in a moment by the electrode-member monitoring unit 27, thereby allowing a concern resulting from the abnormality of the electrode member 3 to be prevented from occurring.

Moreover, in order to output the stimulus signal to the patient, the present embodiment includes the electrode member 3 attached to the patient. This electrode member 3 is composed of the electrodes 41A, 41B to which the stimulus signal is supplied; and the adhesive cover member 52 to which the electrodes 41A, 41B are attached. The cover member 52 is made up of, e.g., the moisture-permeable unwoven cloth.

In this case, the electrode member 3 is used by sticking to the patient the cover member 52 that is adhesive. If the cover member 52, however, is not breathable, a steamed condition due to perspiration makes it easy for the cover member 52 to be peeled off. By allowing the cover member 52 to have an appropriate moisture permeability, reduced is an uncomfortable feeling such as the steamed condition and an itching condition.

Besides, in the present embodiment, in order to output the stimulus signal to the patient, the apparatus 1 includes the planar electrode member 3 that is attached to the patient. The electrode member 3 is composed of the electrodes 41A, 41B to which the stimulus signal is supplied; and the cover member 52 to which the electrodes 41A, 41B are attached. Between a pair of the electrodes 41A, 41B, the cover member 52 is formed with the slit 53, the cutout or the like which act as the vent.

In this case, the electrode member 3 is used by sticking to the patient the adhesive cover member 52. However, in consideration of attaching the planar electrode member 3 to a three-dimensional portion, the cover member 52 is formed with the vent such as the slit 53, the cutout or the like to make it easy for the electrode member 3 to be three dimensionally bended. Consequently, an uncomfortable coarse feeling felt at the time of attaching the electrode member 3 can be reduced. Further, the perspiration and the steamed condition are eliminated through the vent when using the electrode member 3, and the electrode member 3 that is easily bendable can be easily peeled off after use.

Further, in the present embodiment, the apparatus 1 includes a pair of the flexible cords 2A, 2B for electrically connecting the stimulus generating unit 51 to the electrodes 41A, 41B of the electrode member 3. The aforementioned electrode member 3 is composed of a pair of the electrodes 41A, 41B to which the stimulus signal is supplied; and the adhesive cover member 52 to which the electrodes 41A, 41B are attached. Especially as shown in FIG. 3, a pair of the cords 2A, 2B is drawn from different sides of the pair of the electrodes 41A, 41B, respectively.

In this case, the conductor unit 3 is used by sticking to the patient the adhesive cover member 52. When drawing the cords 2A, 2B from the same side of the pair of the electrodes 41A, 41B, the pull force from the electrodes 2A, 2B is applied to the same side of the electrode member 3 to make it easy for the electrode member 3 to be peeled off the patient. Hence, the cords 2A, 2B are drawn from the different sides of the pair of the electrodes 41A, 41B in a manner such that the pull forces from the electrodes 2A, 2B are applied to the different sides of the electrode member 3, thereby making it possible to prevent the electrode member 3 from being peeled off due to the pull forces of the cords 2A, 2B Furthermore, in the present embodiment, the stimulus generating unit 51 is so configured that the stimulus signal is applied to the patient for a prolonged time everyday.

In this case, the apparatus 1 is used everyday to continuously and repeatedly perform the exercise (EMS) due to the electric stimulus, thereby also eventually allowing the slimming effect of the patient to be expected.

The present invention is not limited to the above each embodiment and various modifications are possible within the gist of the present invention For example, the stimulus generating unit 51 for outputting a desired stimulus signal to the electrode member may be configured as a system different from the one employing the FETs 36, 37 and the transformer 38, as shown in the present embodiment. Besides, the control CPU 21 and the waveform producing CPU 32 may be combined together as one CPU. Further, the on time and off time of an individual electric pulse may be set such that an capacitor action of a human body is utilized and thereby the stimulus signal is made into a triangular waveform and various distorted waveforms. Otherwise, electric pulses may be generated at random during the conduction period of the stimulus signal.

What is claimed:

1. A respiratory abnormality improvement apparatus for applying to a patient a stimulus signal as an electric stimulus, comprising:
  a stimulus generating unit for generating the stimulus signal; and
  a detection unit for detecting a respiratory condition of the patient, wherein said stimulus signal includes:
    a first stimulus signal element at a first current level; and
    a second stimulus signal element at a second current level different than the first current level, based on a detection signal from said detection unit when the patient is determined to be under a respiratory abnormality condition, and wherein each of said first and second stimulus signal elements occurs in a recurring manner and includes:
      a conduction period generating an electric pulse group having a current level higher than a given level; and
      a break period generating an electric pulse group having a current level not higher than the given level or generating no electric pulse group, and wherein
      each conduction period includes:
        a first interval allowing the current level of said stimulus signal to rise in a manner that a rate of increase becomes gradually moderate with time;
        a second interval following said first interval and allowing the current level of said stimulus signal to remain constant; and
        a dither provided in said first or second interval of the conduction period, said dither causing the current level and/or a frequency of said stimulus signal to repeatedly increase and decrease multiple times within each conduction period which begins with a start of the first interval and finishes with a lapse of the second interval.

2. The respiratory abnormality improvement apparatus according to claim 1, wherein said stimulus generating unit is configured in a manner such that during said break period, the current level of said stimulus signal is lowered to within a range from 0 to a value that causes no muscle tension on the patient.

3. The respiratory abnormality improvement apparatus according to claim 2, wherein said stimulus generating unit is configured in a manner such that during said conduction period at the time of generating said first stimulus signal element, said dither is not provided in said first interval, but only in said second interval; and that during said conduction period at the time of generating the second stimulus signal element, said dither is provided therein from during the first interval through said second interval.

4. The respiratory abnormality improvement apparatus according to claim 2, wherein said stimulus generating unit is configured in a manner such that during said conduction period at the time of generating said first stimulus signal element, said dither is not provided in said first interval, but only in said second interval; and that during said conduction period at the time of generating the second stimulus signal element, said dither is provided therein from during the first interval through said second interval.

5. The respiratory abnormality improvement apparatus according to claim 1, wherein said stimulus generating unit is configured in a manner such that during a period in which said dither is provided, the current level of said stimulus signal rises in a manner such that a rate of increase becomes gradually moderate with time.

6. The respiratory abnormality improvement apparatus according to claim 5, wherein said stimulus generating unit is configured in a manner such that during said dither provision at the time of generating said first stimulus signal element, the frequency of said stimulus signal repeatedly increases and decreases only in a period in which the current level of said stimulus signal rises.

7. The respiratory abnormality improvement apparatus according to claim 5, wherein said stimulus generating unit is configured in a manner such that during said dither provision period at the time of generating said second stimulus signal element, the frequency of said stimulus signal repeatedly increases and decreases only in a period in which the current level of said stimulus signal is maintained constant before rising.

8. The respiratory abnormality improvement apparatus according to claim 1, further comprising:

an electrode member configured to be attached to the patient and used to output said stimulus signal to the patient; and an electrode-member monitoring unit for detecting an abnormal condition by monitoring a current and a voltage that are applied to said electrode member.

9. The respiratory abnormality improvement apparatus according to claim 1, further comprising:

an electrode member configured to be attached to the patient and used to output said stimulus signal to the patient, said electrode member including:

at least one electrode to which said stimulus signal is supplied; and a moisture permeable material-made adhesive cover member to which said electrode is attached.

10. The respiratory abnormality improvement apparatus according to claim 1, further comprising:

an electrode member configured to be attached to the patient and used to output said stimulus signal to the patient, said electrode member including:

at least one electrode to which said stimulus signal is supplied; and a vented adhesive cover member to which said electrode is attached.

11. The respiratory abnormality improvement apparatus according to claim 1, further comprising:

an electrode member configured to be attached to the patient and used to output said stimulus signal to the patient; and a pair of cords connecting said stimulus generating unit and said electrode member, wherein said electrode member includes: a pair of electrodes to which said stimulus signal is supplied; and an adhesive cover member to which said electrodes are attached, and wherein the pair of said cords are drawn from different sides of the pair of said electrodes.

12. The respiratory abnormality improvement apparatus according to claim 1, wherein said stimulus generating unit is configured in a manner such that said stimulus signal is capable of being applied to the patient every day.

* * * * *